United States Patent
Morone et al.

(10) Patent No.: US 11,485,719 B2
(45) Date of Patent: Nov. 1, 2022

(54) WATER SOLUBLE 3-KETOCOUMARINS

(71) Applicant: IGM RESINS ITALIA S.R.L., Milan (IT)

(72) Inventors: Marika Morone, Lipomo CO (IT); Vincenzo Razzano, Siena SI (IT); Stephen Postle, Glen Rock, NJ (US); Gabriele Norcini, Comabbio (IT)

(73) Assignee: IGM RESINS ITALIA S.R.L., Milan (IT)

( * ) Notice: Subject to any disclaimer, the term of this patent is extended or adjusted under 35 U.S.C. 154(b) by 319 days.

(21) Appl. No.: 16/772,395

(22) PCT Filed: Dec. 6, 2018

(86) PCT No.: PCT/IB2018/059703
§ 371 (c)(1),
(2) Date: Jun. 12, 2020

(87) PCT Pub. No.: WO2019/116177
PCT Pub. Date: Jun. 20, 2019

(65) Prior Publication Data
US 2021/0070726 A1    Mar. 11, 2021

Related U.S. Application Data

(60) Provisional application No. 62/598,655, filed on Dec. 14, 2017.

(51) Int. Cl.
| | | |
|---|---|---|
| *C09D 11/101* | (2014.01) | |
| *C08F 2/48* | (2006.01) | |
| *C07D 405/10* | (2006.01) | |
| *C07D 311/16* | (2006.01) | |
| *C09D 11/38* | (2014.01) | |
| *C08F 2/50* | (2006.01) | |
| *B41J 2/01* | (2006.01) | |

(52) U.S. Cl.
CPC .......... *C07D 311/16* (2013.01); *C07D 405/10* (2013.01); *C08F 2/48* (2013.01); *C09D 11/101* (2013.01); *C09D 11/38* (2013.01); *B41J 2/01* (2013.01); *C08F 2/50* (2013.01)

(58) Field of Classification Search
CPC ....... C07D 311/16; C07D 405/10; C08F 2/48; C08F 2/50; C09D 11/101; C09D 11/38; B41J 2/01
See application file for complete search history.

(56) References Cited

U.S. PATENT DOCUMENTS

| | | | |
|---|---|---|---|
| 4,602,097 A | 7/1986 | Curtis | |
| 2008/0239045 A1* | 10/2008 | Umebayashi | C09D 11/101 522/63 |
| 2017/0107386 A1 | 4/2017 | Herlihy et al. | |

FOREIGN PATENT DOCUMENTS

| | | | | |
|---|---|---|---|---|
| CN | 107 915 701 | | 4/2018 | |
| CN | 107915701 A | * | 4/2018 | ........... C07D 215/54 |
| EP | 0 022 188 | | 1/1981 | |
| GB | 2108487 | | 5/1983 | |
| WO | 2014/063997 | | 5/2014 | |
| WO | WO-2014063997 A1 | * | 5/2014 | ........... A61K 6/0052 |
| WO | 2014/095724 | | 6/2014 | |
| WO | 2017/216699 | | 12/2017 | |
| WO | WO-2017216699 A1 | * | 12/2017 | ........... C07D 311/16 |

OTHER PUBLICATIONS

International serch report and writen opinion issued by the EPO for PCT/IB2018/059703 dated Apr. 9, 2019.

Niu Handong et al : "A novel structural class of coumarin-chalcone fibrates as PPAR [al pha]/[garmia]agonists with potent anti oxidant activities: Design, synthesis,biologicaL evaluation and molecular docking studies", European Journal of Medicinal Chemistry,Editions Scientifique Elsevier, Paris, FR, vol. 138, Jun. 22, 2017 (Jun. 22, 2017), pp. 212-220.

* cited by examiner

*Primary Examiner* — Yaovi M Ameh
(74) *Attorney, Agent, or Firm* — Silvia Salvadori

(57) ABSTRACT

The present invention relates to novel 3-ketocoumarins with improved water compatibility, which are useful as photoinitiators and to compositions comprising said photoinitiators. The invention also relates to compositions comprising said novel 3-ketocoumarins and to a process for photopolymerizing comprising them.

20 Claims, No Drawings

WATER SOLUBLE 3-KETOCOUMARINS

This application is a U.S. national stage of PCT/IB2018/059703 filed on 6 Dec. 2018, which claims priority to and the benefit of U.S. Provisional Application No. 62/598,655 filed 14 Dec. 2017, the contents of which are incorporated herein by reference in their entireties.

TECHNICAL FIELD

The present invention relates to novel 3-ketocoumarins with improved water compatibility, which are useful as photoinitiators and to compositions comprising said photoinitiators. The invention also relates to compositions comprising said novel 3-ketocoumarins and to a process for photopolymerizing comprising them.

TECHNICAL BACKGROUND

Photoinitiators used in radiation curable coatings need to have good cure speed, in particular good surface curing, low odour and low yellowing. When photoinitiators are used in water based formulations, need also to: be compatible or soluble in water, have low steam volatility (the coating process may involve a pre-dry step where high temperatures are used to remove water), be effective in photocrosslinking of the resins to produce the desired polymeric surface coating, be safe and non-toxic chemicals.

Among the light radiation sources used in this field, light emitting diodes (LED), a semiconductor light source, have been the subject of significant development over the past few years because of the advantages of low temperature operation and extremely long life in comparison with conventional medium pressure mercury arc curing lamps. LED lamps are advantageous because of the inherently small size of LED units, their longer lifetime, their robustness and their ability to be easily engineered, for example into commercial printing systems.

When using LED lamps to photocure inks and coatings, it is necessary to use selected photoinitiator systems that are tuned to the wavelength of this light source. While Mercury arc lamps typically have a polychromatic emission spectrum, emitting light in all regions of the UV-visible spectrum from 200 to 450 nm, LED lamps usually have only a single emission band in the range 365-420 nm.

Photoinitiators, absorbing in the region from 365 nm to 420 nm, are thus required to make full use of the recent development of LEDs with increasing power. Moreover, since high concentration of photoactive substance are usually required for LED applications, the photoinitiators should have a high compatibility with the photopolymerizable system.

Thioxanthones, such as isopropyl thioxanthone (ITX) and its derivatives, and acyl phosphine oxides are photoinitiators commonly used in this field.

U.S. Pat. No. 4,602,097 (Ulano Corporation), GB 2108487 (Sericol Group) and US 2017/017386 (Sun Chemical Group) disclose water soluble thioxantones, unfortunately, the compounds belonging to this class are prone to yellowing upon exposure, thereby forming degradation products with limited stability. As a result, the original yellowing can shift unpredictably upon storage. Especially in imaging, e.g. inkjet printing, this unstable yellowing behavior makes quite difficult the control of the image tone in the final image.

WO2014/095724 discloses water soluble bisacylphosphine oxides initiators, unfortunately, this class of molecules result in medium volatile aldehyde type of degradation products, producing a background smell of the cured coatings or the printed.

A commercial product belonging to the bisacylphosphine oxides class is Omnirad 819 DW, supplied by IGM Resins BV, which is a dispersion of bis(2,4,6-trimethylbenzoyl) phenyl phosphine oxide (Omnirad 819, supplied by IGM Resins BV) in water. However, the use of dispersant agent is not acceptable in all applications, either because dispersant agents can migrate through the cured film and have deleterious effects e.g. they can plasticize the cured film, rendering it less fit for purpose, or they can contaminate a foodstuff in contact with said cured film.

That means that there continues to be a demand for other water compatible photoinitiators having improved reactivity with LED lamps.

SUMMARY OF THE INVENTION

The present invention relates to a new class of 3-ketocoumarins, especially suitable for water based radiation curable compositions and methods for preparing said photoinitiators.

The compounds of the present invention comprise 3-ketocoumarins properly functionalized to show enhanced compatibility in water based compositions. sulfate Indeed, we have now discovered a series of novel compounds based on 3-ketocoumarins which overcome the drawbacks of the prior art compounds, i.e. which have good compatibility in water based formulations, high reactivity, low yellowing and give cured products which have extremely low odor.

DESCRIPTION OF THE INVENTION

According to a first of its aspects, the present invention relates to a 3-ketocoumarin of Formula (I):

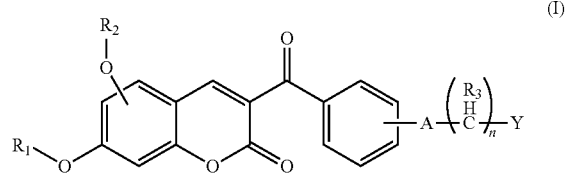

wherein:

$R_1$, $R_2$ are, each independently, hydrogen; $C_1$-$C_{12}$ alkyl; substituted or unsubstituted aryl; substituted or unsubstituted heteroaryl; substituted or unsubstituted $C_5$-$C_6$ cycloalkyl; or $C_1$-$C_{12}$ alkyl which is substituted with SH, —N(alkyl $C_1$-$C_6$)$_2$, piperidino, morpholino, piperazino, —OH, —O(alkyl $C_1$-$C_{12}$), —COOH; or $C_1$-$C_{12}$ alkoxy;

n is an integer number from 0 to 10 and when n is 0 A is directly linked to Y;

A represents CHR$_3$, O, S or NR$_4$ where R$_4$ is hydrogen or an alkyl $C_1$-$C_6$ group;

R3 is hydrogen; $C_1$-$C_{12}$ alkyl; substituted or unsubstituted aryl; substituted or unsubstituted heteroaryl; substituted or unsubstituted $C_5$-$C_6$ cycloalkyl; or $C_1$-$C_{12}$ alkyl which is substituted with SH, —N(alkyl $C_1$-$C_6$)$_2$, piperidino, morpholino, piperazino, —OH, —O(alkyl $C_1$-$C_{12}$), —COOH; or $C_1$-$C_{12}$ alkoxy;

Y is selected from:

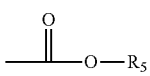

wherein $R_5$ is a substituted or unsubstituted $C_1$-$C_{50}$ alkyl group which is interrupted by one or more oxygens and may terminate with a hydroxy group or with an alkyl residue;

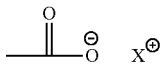

wherein X is an inorganic or organic cation;

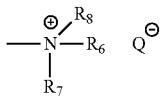

wherein Q is an inorganic or organic anion and $R_6$, $R_7$ and $R_8$ are, each independently, hydrogen; $C_1$-$C_{12}$ alkyl; substituted or unsubstituted aryl; substituted or unsubstituted heteroaryl; substituted or unsubstituted $C_5$-$C_6$ cycloalkyl; $C_1$-$C_{12}$ alkyl which is substituted with SH, —N(alkyl $C_1$-$C_6$)$_2$, piperidino, morpholino, piperazino, —OH, —O(alkyl $C_1$-$C_{12}$), —COOH; $C_1$-$C_{12}$ alkoxy; or two of R6, R7 and R8, form a mono cyclic ring structure,

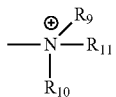

wherein $R_9$, $R_{10}$ and $R_{11}$ are each independently one of another hydrogen, alkyl $C_1$-$C_{12}$, substituted or unsubstituted phenyl, aryl or heteroaryl, cycloalkyl $C_5$-$C_6$, alkyl $C_1$-$C_{12}$ which is substituted with SH, —N(alkyl $C_1$-$C_6$)$_2$, piperidino, morpholino, piperazino, —OH, —O(alkyl $C_1$-$C_{12}$), —COOH; $C_1$-$C_{12}$ alkoxy; or two of $R_9$, $R_{10}$ and $R_{11}$, form a mono cyclic ring structure, and at least one of $R_9$, $R_{10}$ or $R_{11}$ is selected from the following:

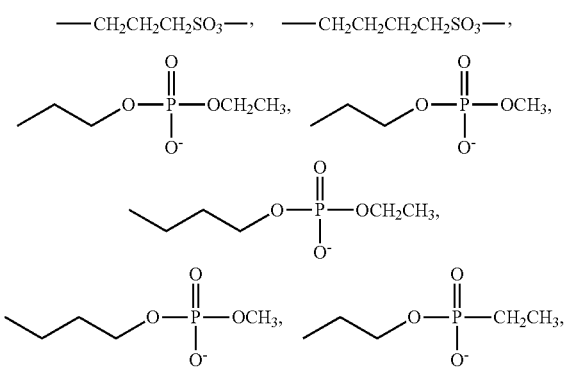

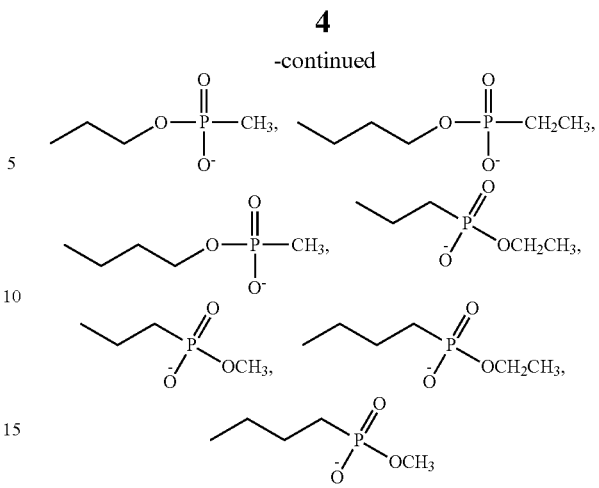

DETAILED DESCRIPTION OF THE INVENTION

According to preferred embodiments of the invention, A is $CHR_3$ or an oxygen, more preferably A is $CHR_3$.

According to preferred embodiments of the invention, in Formula (I) n is from 0 to 6, more preferably n is from 1 to 4.

According to preferred embodiments of the invention in Formula (I) Y is

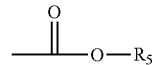

wherein R5 is a substituted or unsubstituted $C_1$-$C_{50}$ alkyl group which is interrupted by one or more oxygen and may terminate with a hydroxy group or with an alkyl residue.

According to preferred embodiments of the invention, X is an organic or inorganic cation for example selected from metals, such for example alkaline metals, alkaline earth metals, e.g. Li, Na, K, Cs and the like.

According to other preferred embodiments of the invention, X is selected from "onium" cations, such as an ammonium-, phosphonium-, iodonium- or sulfonium cations.

Onium cations include for example ammonium, tetra-alkylammonium, tri-alkyl-aryl-ammonium, di-alkyl-di-aryl-ammonium, tetra-aryl-ammonium, tetra-alkylphosphonium, tri-alkyl-aryl-phosphonium, di-alkyl-di-aryl-phosphonium, tri-aryl-alkyl-phosphonium, tetra-aryl-phosphonium.

Exemplary onium cations $N^+R_{12}R_{13}R_{14}R_{15}$ or $P^+R_{12}R_{13}R_{14}R_{15}$, wherein $R_{12}$, $R_{13}$, $R_{14}$, $R_{15}$ each independently are selected from hydrogen, $C_1$-$C_{20}$ alkyl, phenyl; $C_1$-$C_{20}$ alkyl substituted by OH or phenyl; and phenyl substituted by OH or $C_1$-$C_4$ alkyl; or two of $R_{12}$, $R_{13}$, $R_{14}$ and $R_{15}$ form a mono- or bicyclic-ring structure.

Examples for X as $N^+R_{12}R_{13}R_{14}R_{15}$ and two of $R_{12}$, $R_{13}$, $R_{14}$ and $R_{15}$ forming a mono or bicyclic ring structure are the following:

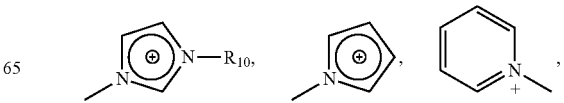

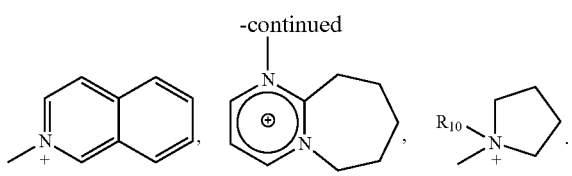

According to a preferred embodiment of the invention, X is preferably $Li^+$, $Na^+$, $K^+$, $N^+R_{12}R_{13}R_{14}R_{15}$ or $P^+R_{12}R_{13}R_{14}R_{15}$, more preferably $Li^+$, $Na^+$, $K^+$ or $N^+R_{12}R_{13}R_{14}R_{15}$.

According to other preferred embodiments of the invention, Q is an inorganic or organic anion such as for instance, $Cl^-$, $Br^-$, $I^-$, phosphate, phosphite, sulfate and sulphite ....

More preferably $R_1$, $R_2$ are each independently a C1-C12 alkyl group, more preferably a $C_1$-$C_4$ alkyl group.

In the present text the expressions "alkyl" or "alkyl group" mean, where not differently indicated, a linear or branched alkyl chain containing from 1 to 12 carbon atoms and includes all possible variants for each number of carbon atoms in the alkyl group i.e. for three carbon atoms: n-propyl and isopropyl; for four carbon atoms: n-butyl, isobutyl and tertiary-butyl; for five carbon atoms: n-pentyl, 1,1-dimethylpropyl, 2,2-dimethylpropyl and 2-methyl-butyl, etc.

The expressions "cycloalkyl" or "cycloalkyl group" include, where not differently indicated, an aliphatic ring preferably containing from 5 to 6 carbon atoms, which can be cyclopentyl, cyclohexyl. Preferably the cycloalkyl group is not substituted.

The expressions "aryl" or "aryl group" include for example substituted or unsubstituted phenyl group, substituted or unsubstituted naphthyl group, anthracenyl group, indenyl group, fluorenyl group and the like.

The expressions "heteroaryl" or "heteroaryl group" include for example furan, thiophene, pyrrole, oxazole, isooxazole, thiazole, isothiazole, imidazole, pyrazole, pyrane, pyridine, pyrrolidine, piperidine, indole, quinoline, isoquinoline, xanthene, carbazole, acridine, indoline, julolidine and the like.

The expression "$C_1$-$C_{50}$ alkyl group which is interrupted by one or more oxygens" means that said oxygen atoms are separated from one another by at least one methylene group, i.e. the O atoms are non-consecutive. Examples are the following structural units —O—CH$_2$—OCH$_3$, —O—CH$_2$CH$_2$—OCH$_2$CH$_3$, —O—CH$_2$CH$_2$—OCH$_2$CH$_3$—OH, —O—[CH$_2$CH$_2$O]$_v$CH$_3$ or —O—[CH$_2$CH$_2$O]$_v$OH or —O—[CH$_2$CH$_2$O]$_v$CH$_2$CH$_3$ with v=1-24, —O—[CH$_2$CH$_2$CH$_2$O]$_p$OH or —O—[CH$_2$CH$_2$CH$_2$O]$_p$CH$_3$ or —O—[CH$_2$CH$_2$CH$_2$O]$_p$CH$_2$CH$_3$ with p=1-16.

The term "substituted" means that a substituent is present; said substituent include a halogen atom, alkyl, cycloalkyl, alkoxy, alkylamino, dialkylamino, alkylthio or arylthio group, heterocyclic groups; preferably, said substituent is selected from methyl, ethyl, isopropyl, tert-butyl, phenyl, trifluoromethyl, cyano, acetyl, ethoxycarbonyl, carboxyl, carboxylate, amino, methylamino, dimethylamino, ethylamino, diethylamino, isopropylamino, diisopropylamino, cyclohexylamino, dicyclohexylamino, acetylamino, piperidino, pyrrolidyl, methoxy, ethoxy, propoxy, isopropoxy, butoxy, pentyloxy, phenoxy, hydroxyl, acetoxy, —PO$_3$H, methylthio, ethylthio, i-propylthio, n-propylthio, phenylthio, mercapto, acetylthio, thiocyano, methylsulfinyl, methylsulfonyl, dimethylsulfonyl, sulfonate groups, fluorine atom, chlorine atom, bromine atom, iodine atom, trimethylsilyl, triethylsilyl, trimethylstannyl, furyl, thienyl, pyridyl, piperidino, morpholino, pyrrolidyl groups and on the like.

According to a preferred embodiment, $R_1$ and $R_2$ are the same and represent $C_1$-$C_4$ alkyl, advantageously methyl. According to a preferred embodiment, $OR_2$ is in 5-position.

According to a preferred embodiment, A is in 4-position (i.e. in para-position respect to the carbonyl group).

Preferably $R_3$ is hydrogen.

The compounds represented by Formula (I) can be prepared according to conventional methods known to the skilled in the art. For example representative derivatives can be synthesized as follows

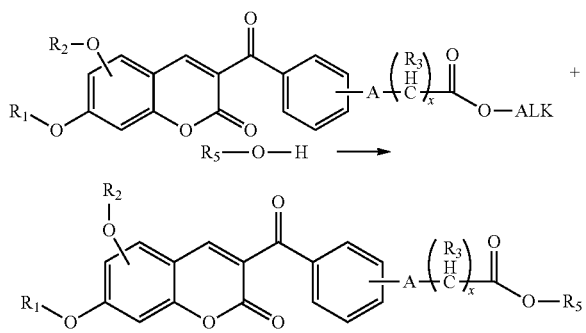

wherein ALK is an alkyl group, preferably a $C_1$-$C_{12}$ alkyl group, for example methyl or ethyl, and $R_1$, $R_2$, $R_3$ and $R_5$ are as described above.

More details relating to the synthesis of representative compounds of the invention are reported in the Experimental Section of the present description.

The process for the preparation of the compounds of Formula (I) described above is a further subject-matter of the invention. Other synthesis routes can anyway be used.

The compounds of Formula (I) are useful as photoinitiators. The use of the compounds of Formula (I) as photoinitiators in photopolymerization processes is a further subject-matter of the present invention, as well as a method for light curing which comprises using the compounds of Formula (I) as photoinitiators.

Another subject-matter of the invention is the use of compounds of Formula (I) in a polymerization process for the curing of an ink, of a coating or a three-dimensional assembly.

For "photoinitiator" we mean a molecule that possesses a functional group able to generate radicals (alone or in combination with a co-initiator) capable of starting a polymerization by exposure to light with an appropriate wavelength.

Compounds of Formula (I) are useful, in particular, in water based photopolymerizable compositions suitable for inks and coatings that can be photopolymerized by exposure to a radiation source.

For their use, compounds of Formula (I) are included in photopolymerizable compositions which comprise (a) at least one ethylenically unsaturated compound dissolved or emulsified in water and (b) at least one compound of Formula (I).

By "ethylenically unsaturated" compound we mean a monomer, oligomer, prepolymer having at least one unsaturated double bond, or a mixture thereof, capable of undergoing radical polymerization. Also monomers, oligomers and prepolymers combinations with different degrees of unsaturation can be used.

The photopolymerizable compositions can also contain other additives normally used in ink and coating compositions. For example, they can contain one or more water compatible solvents, one or more water soluble monomers and one or more additional photoinitiators.

It is understood that the present formulation could contain a wide range of raw materials that are compatible with either or both photocurable and water based compositions. These materials include, but are not limited to, polymers and resins, monomers, oligomers, amine synergists, surface control additives, defoamers, biocides, binders, stabilizers, pH adjusters, surfactants, etc.

The photopolymerizable aqueous prepolymer dispersions are obtainable commercially in many variations. They are to be understood as being a dispersion consisting of water and at least one prepolymer dispersed therein. The concentration of the water in those systems is, for example, from 5 to 80% by weight, especially from 30 to 60% by weight. The photopolymerizable prepolymer or prepolymer mixture is present in concentrations of, for example, from 95 to 20% by weight, especially from 70 to 35% by weight. The sum of the indicated percentages for water and prepolymer in those compositions is in each case 100; auxiliaries and additives, which are present in varying amounts depending on the intended use, are in addition thereto.

The photopolymerizable film-forming prepolymers, which are dispersed or in many cases dissolved in water, are mono- or poly-functional ethylenically unsaturated prepolymers capable of initiation by free radicals and known per se for aqueous prepolymer dispersions; for example, they have a content of from 0.01 to 1.0 mol of polymerisable double bonds per 100 g of prepolymer and an average molecular weight of, for example, at least 400, especially from 500 to 10 000, although depending on the intended use prepolymers having higher molecular weights also come into consideration.

Used are, for example, polyesters containing polymerisable C=C double bonds and having an acid number of at most 10, polyethers containing polymerisable C=C double bonds, hydroxyl-group-containing reaction products of a polyepoxide containing at least two epoxide groups per molecule with at least one α,β-ethylenically unsaturated carboxylic acid, polyurethane (meth)acrylates and also acrylic copolymers containing α,β-ethylenically unsaturated acrylic radicals as described, for example, in EP012339. Mixtures of those prepolymers may also be used. Also suitable are, for example, the polymerisable prepolymers described in EP033896, which are thioether adducts of polymerisable prepolymers having an average molecular weight of at least 600, a carboxyl group content of from 0.2 to 15% and a content of from 0.01 to 0.8 mol of polymerisable C=C double bonds per 100 g of prepolymer. Other suitable aqueous dispersions based on particular (meth) acrylic acid alkyl ester polymerisation products are described in EP041125; suitable water-dispersible, radiation-curable prepolymers obtained from urethane acrylates are to be found in, for example, DE2936039.

The photopolymerisable compounds (a) are used singly or in any desired mixture.

Particularly preferred are the acrylated polyurethane dispersions.

The water based photopolymerizable composition of the present invention preferably comprise from 15 to 40% by weight of an ethylenically unsaturated compound dissolved or emulsified in water, from 0.1 to 10% by weight of a compound of Formula (I), from 20 to 80% by weight of water.

More preferably the water based photopolymerizable composition comprise from 15 to 40% by weight of an ethylenically unsaturated compound dissolved or emulsified in water, from 0.1 to 8% by weight of a compound of Formula (I), from 20 to 75% by weight of water.

Most preferably the water based photopolymerizable composition comprise from 20 to 35% by weight of an ethylenically unsaturated compound dissolved or emulsified in water, from 0.2 to 6% by weight of a compound of Formula (I), from 30 to 70% by weight of water.

Using the expression "by weight", we mean that the value are expressed as percentage weight with respect to the total composition weight.

Besides the above-mentioned compounds, other components normally used in the field and known to the experts in the art can be added to the photopolymerizable compositions of the invention. For example, thermal stabilizers, photo-oxidation stabilizers, anti-oxidants, fillers, dispersants, coloring and/or opacifying substances and other additives of general use.

The photopolymerizable compositions of the invention can also conveniently include other monomers and oligomers commonly used in the field.

Examples of monomers suitable for the realization of the present invention are listed below. This includes both materials that are fully water soluble as therefore easy to use and materials which are insoluble or that have a limited water compatibility, but capable of being use from those skilled in the art. So, suitable monomers are isobutyl acrylate; cyclohexyl acrylate; iso-octyl acrylate; n-octyl acrylate; isodecyl acrylate; iso-nonyl acrylate; octylidecyl acrylate; lauryl acrylate; 2-propyl heptyl acrylate; tridecyl acrylate; hexadecyl acylate; stearyl acrylate; iso-stearyl acrylate; behenyl acrylate; tetrahydrofurfuryl acrylate; 4-t.butyl cyclohexyl acrylate; trimethylcyclohexane acrylate; isobornyl acrylate; dicyclopentyl acrylate; dihydrodicyclopentadienyl acrylate; dicyclopentenyloxyethyl acrylate; dicyclopentanyl acrylate; benzyl acrylate; phenoxyethyl acrylate; 2-hydroxy-3-phenoxypropyl acrylate; alkoxylated nonylphenol acrylate; cumyl phenoxyethyl acrylate; cyclic trimethylolpropane formal acrylate; 2(2-ethoxyethoxy) ethyl acrylate; polyethylene glycol monoacrylate; polypropylene glycol monoacrylate; caprolactone acrylate; ethoxylated methoxy polyethylene glycol acrylate; methoxy triethylene glycol acrylate; tripropyleneglycol monomethyl ether acrylate; diethylenglycol butyl ether acrylate; alkoxylated tetrahydrofurfuryl acrylate; ethoxylated ethyl hexyl acrylate; alkoxylated phenol acrylate; ethoxylated phenol acrylate; ethoxylated nonyl phenol acrylate; propoxylated nonyl phenol acylate; polyethylene glycol o-phenyl phenyl ether acrylate; ethoxylated p-cumyl phenol acrylate; ethoxylated nonyl phenol acrylate; alkoxylated lauryl acrylate; ethoxylated tristyrylphenol acrylate; N-(acryloyloxyethyl)hexahydrophthalimide; N-butyl 1,2 (acryloyloxy) ethyl carbamate; acryloyl oxyethyl hydrogen succinate; octoxypolyethylene glycol acrylate; octafluoropentyl acrylate; 2-isocyanato ethyl acrylate; acetoacetoxy ethyl acrylate; 2-methoxyethyl acrylate; dimethyl arninoethyl acrylate; 2-carboxyethyl acrylate; 4-hydroxy butyl acrylate; 1,3-butylene glycol diacrylate; 1,4-butanediol diacrylate; neopentyl glycol diacrylate; ethoxylated neopentyl glycol diacrylate; propoxylated neopentyl glycol diacrylate; 2-methyl-1,3-propanedlyl ethoxy acrylate; 2-methyl-1,3-propanediol diacrylate; ethoxylated 2-methyl-1,3-propanediol diacrylate; 3 methyl 1,5-pentanedial diacrylate; 2-butyl-2-ethyl-1,3-propanediol diacrylate; 1,6-hexanediol diacrylate; alkoxylated hexanediol diacrylate; ethoxylated hexanediol diacrylate; propoxylated hexanediol diacrylate;

1,9-nonanediol diacrylate; 1,10 decanediol diacrylate; ethoxylated hexanediol diacrylate; alkoxylated hexanediol diacrylate; diethyleneglycol diacrylate; triethylene glycol diacrylate; tetraethylene glycol diacrylate; polyethylene glycol diacrylate; propoxylated ethylene glycol diacrylate; dipropylene glycol diacrylate; tripropyleneglycol diacrylate; polypropylene glycol diacrylate; poly (tetramethylene glycol) diacrylate; cyclohexane dimethanol diacrylate; ethoxylated cyclohexane dimethanol diacrylate; alkoxylated cyclohexane dimethanol diacrylate; polybutadiene diacrylate; hydroxypivalyl hydroxypivalate diacrylate; tricyclodecanedimethanol diacrylate; 1,4-butanediylbis[oxy(2-hydroxy-3,1-propanediyl)]diacrylate; ethoxylated bisphenol A diacrylate; propoxylated bisphenol A diacrylate; propoxylated ethoxylated bisphenol A diacrylate; ethoxylated bisphenol F diacrylate; 2-(2-Vinyloxyethoxy)ethyl acrylate; dioxane glycol diacrylate; ethoxylated glycerol triacrylate; glycerol propoxylate triacrylate; pentaerythritol triacrylate; trimethylolpropane triacrylate; caprolactone modified trimethylol propane triacrylate; ethoxylated trimethylolpropane triacrylate; propoxylated trimethylol propane triacrylate; tris (2-hydroxy ethyl) isocyanurate triacrylate; e-caprolactone modified tris (2-hydroxy ethyl) isocyanurate triacrylate; melamine acrylate oligomer; pentaerythritol tetraacrylate; ethoxylated pentaerythritol tetraacrylate; di-trimethylolpropane tetra acrylate; dipentaerythritol pentaaacrylate; dipentaerythritol hexaaacrylate; ethoxylated dipentaerythritol hexaacrylate; combinations thereof; and the like.

Other monomers include cyclic lactam such as N-vinyl caprolactam, N-vinyl oxazolidinone and N-vinyl pyrrolidone, and secondary or tertiary acrylamides such as acryloyl morpholine, diacetone acrylamide, N-methyl acrylamide, N-ethyl acrylamide N-isopropyl acrylamide, N-t-butyl acrylamide, N-hexyl acrylamide, N-cyclohexyl acrylamide, N-octyl acrylamide, N-t-octyl acrylamide, N-dodecyl acrylamide, N-benzyl acrylamide, N-(hydroxymethyl)acrylamide, N-isobutoxymethyl acrylamide, N-butoxymethyl acrylamide, N,N-dimethyl acrylamide, N,N-diethyl acrylamide, N,N-propyl acrylamide, N,N-dibutyl acrylamide, N,N-dihexyl acrylamide, N,N-dimethylamino methyl acrylamide, N,N-dimethylamino ethyl acrylamide, N,N-dimethylamino propyl acrylamide, N,N-dimethylamino hexyl acrylamide, N,N-diethylamino methyl acrylamide, N,N-diethylamino ethyl acrylamide, N,N-diethylamino propyl acrylamide, N,N-dimethylamino hexyl acrylamide, and N,N'-methylenebisacrylamide, and the like.

Monomers, oligomers and prepolymers, which are commonly used in water based photopolymerizable composition are preferred. These compounds are well known to the expert in the art and are described for example in US2017/0107386, WO2015/197472, WO2017/053178, WO2014/095724.

The monomer is added to the composition in an amount of 0 to 20%, preferably 1 to 15 wt %, more preferably 1 to 10 wt %, and most preferably 2 to 5 wt % based on the total weight of the photopolymerizable composition.

The water based photopolymerizable composition preferably contains at least one organic solvent, preferably one or more water compatible organic solvents. As will be understood, organic solvents are not radiation curable and may serve several purposes. For example, an organic solvent may help to solubilize one or more of the composition components.

Suitable organic solvents include triacetin, N-methyl-2-pyrrolidone, 2-pyrrolidone, glycerol, urea, thiourea, ethylene urea, alkyl urea, alkyl thiourea, dialkyl urea and dialkyl thiourea, diols, including ethanediols, propanediols, propanetriols, butanediols, pentanediols, and hexanediols; glycols, including propylene glycol, polypropylene glycol, ethylene glycol, polyethylene glycol, diethylene glycol, diethylene glycol monopropyl ether, dipropylene glycol ethyl ether, dipropylene glycol methyl ether, tetraethylene glycol and mixtures and derivatives thereof.

Preferred organic solvents comprise water-miscible amides, e.g. optionally substituted cyclic and/or straight chain water-miscible amides and combination comprising two or more thereof.

Examples of suitable amides include pyrrolidones (e.g. 2-pyrrolidone), N-alkyl pyrollidones (e.g. N-ethyl pyrrolidone), N,N-dialkyl alkylamides (e.g. N,N-dimethyl ethylamide), alkoxylated N,N-alkyl alkylamides (e.g. 3-methoxy-N,N-dimethylpropanamide) and mixtures comprising two or more thereof.

The at least one organic solvent is added to the composition in an amount of 0 to 40%, preferably 0.1 to 38 wt %, more preferably 1 to 30 wt %, and most preferably 3 to 25 wt % based on the total weight of the photopolymerizable composition.

The photopolymerizable compositions of the invention can also conveniently include other photoinitiators commonly used in the field.

Suitable further photoinitiators that can be used in combination with the 3-ketocoumarins of Formula (I) are listed below. These include photoinitiators fully or partially soluble in water and photoinitiators that are not water soluble and therefore difficult to use at high level. Examples of photoinitiators are lithium- and magnesium phenyl-2,4,6-trimethylbenzoylphosphinates, 2-4-diethylthioxanthone, isopropylthioxanthone, 2-chlorothioxanthone, 1-chloro-4-propoxythioxanthone, bis dialkylamino benzophenones such as 4 4,4-bis(diethylamino)benzophenone; anthraquinones such as 2-ethyl anthraquinone; and commercially available photoinitiators include Omnirad 4265, Omnirad 819, Omnirad 819DW, Omnirad TPO, Omnirad TPO-L, Omnirad 500, Omnirad 754, Omnirad 2959, Omnirad 910 and Omnirad 2100, Esacure KTO 46, Esacure DP250, Omnipol TX from IGM Resins B. V.; and Genocure™ MBF, GENOPOL TX1 and Nuvapol™ PI 3Q00 from RAHN; and SPEEDCURE 7010 from Lambson; and the like.

Other further photoinitiators that can be used are described in Industrial Photoinitiator, Chapter 4 from CRC Press 2010, Radiation Curing in Polymer Science and Technology, 2, 375-434 (1993), Journal of Polymer Science: Part A: Polymer Chemistry, 40, 504-1518 (2002) and references cited therein, Surface Coatings International, 83(6), 297-303 (2000)), Macromolecular Chemistry and Physics, 209(15), 1593-1600 (2008), JP2007-125381 (Konica Minolta Holdings, Inc.), WO2014/095724 (BASF SE), WO2015/197472 (AGFA Graphics NV), WO2017/053178 and US2017/0107386 (SUN Chemical Corporation).

The additional photoinitiator is added to the composition in an amount of 0 to 10%, preferably 0.1 to 5 wt %, more preferably 0.2 to 3 wt %, and most preferably 0.5 to 2.5 wt % based on the total weight of the photopolymerizable composition.

The photopolymerizable compositions of the invention can also conveniently include a co-initiator, which is a molecule that acts as hydrogen donor that increases the polymerization rate. The co-initiators are known in the art and they are typically alcohols, thiols, amines or ethers that have an available hydrogen, bonded to a carbon adjacent to the heteroatom. Such co-initiators are generally present in an amount from 0.2 to 15% by weight, preferably from 0.2 to 8% by weight. Suitable co-initiators include, but are not limited to, aliphatic, cycloaliphatic, aromatic, aryl-aliphatic, heterocyclic, oligomeric or polymeric amines. They can be primary, secondary or tertiary amines, for example butyl amine, dibutyl amine, tributyl amine, ciclohexyl amine, benzyldimethyl amine, di-cyclohexyl amine, N-phenyl glycine, triethyl amine, phenyl-diethanol amine, triethanolamine, N-methyl ethanolamine, N,N-dimethylethanolamine, piperidine, piperazine, morpholine, pyridine, quinoline, esters of dimethylamino benzoic acid, Michler's ketone (4,4'-bis-dimethyl aminobenzophenone) and corresponding derivatives, ethyl-4-(dimethylamino)benzoate, 2-ethylhexyl-4-(dimethylamino)benzoate, 2-(dimethylamino)ethylbenzoate, and polymeric aminobenzoates such as OMNIPOL ASA from IGM Resins, GENOPOL AB1/AB2 from Rahn, and SPEEDCURE 7040 from Lambson, combinations thereof, and the like.

The use of co-initiators with both tertiary amine and acidic functionalities is also possible, examples are N-phenylglycine derivatives, N,N-dialkylglycine derovatives and 4-dialkylaminobenzoic acid derivatives or salts thereof.

As the amine co-initiator, an amine-modified acrylate compound can be used, examples of such amine-modified acrylate include acrylates modified by reaction with a primary or secondary amine such as EBECRYL 80/81/83/85/880/841/7100/P116, and EBECRYL LEO 10551/10552/10553, available from Alinex; CN 501/550/3705/3715/3735/3755/381/386 and UVA421, all available from Sartomer; Photomer 4250/4967/4775/4969/5006/5662/5930/5960, all available from IGM Resins; GENOMER 5142, 5161, 5171 and 5275 from Rahn; LAROMER LR8996, LR8997, LR8869, LR8889, PO 83F, PO 84F and PO 94F all available from BASF and combination thereof, and the like.

Others amine-modified acrylate are described in U.S. Pat. No. 3,844,916, EP 280222, U.S. Pat. Nos. 5,482,649, 5,734,002 or US2013/0012611.

Preferred co-initiators are 2-ethylhexyl-4-dimethylaminobenzoate, 4-dimethylaminobenzoic acid and N-phenyl glycine.

Other photoinitiators, co-initiators and further components that may be comprised in the composition of the invention are described for example in the documents US2017/0107386, WO2015/197472, WO2017/053178, WO2014/095724 mentioned above.

The compounds of Formula (I) work both in transparent water based photopolymerizable compositions and in non-transparent or colored water based compositions and, in particular, are useful for the preparation of water based photopolymerizable inks. The photoinitiators and the compositions of the invention are particularly suited for the preparation of water based photopolymerizable inks for ink-jet printing.

For this reason, the photopolymerizable composition of the invention can further comprise one or more colorants.

Colorants which can be used in the photopolymerizable inks of the invention are dyes, pigments or a combination thereof. Organic and/or inorganic pigments may be used. The colorants are preferably pigments or polymeric dyes, most preferably pigments. The pigments may be black, white, cyan, magenta, yellow, red, orange, violet, blue, green, brown, mixtures thereof, and the like, as well as other conventional pigments, well known to the skilled in the art.

Exemplary organic pigments include insoluble azo pigments, condensed azo pigments, azo lake, and chelate azo pigments; polycyclic pigments, such as phthalocyanine pigments, perylene and perinone pigments, anthraquinone pigments, quinacridone pigments, dioxane pigments, thioindigo pigments, isoindolinone pigments, and quinophthalone pigments; dye chelates, such as basic dye chelates and acid dye chelates; dye lakes, such as basic dye lakes and acid dye lakes; and nitro pigments, nitroso pigments, aniline black, and fluorescent pigments.

Colorants for ink-jet printing are particularly preferred.

The water based photopolymerizable compositions are generally alkaline. Preferably the pH of the composition is from 7.0 to 9.5.

The photocurable compositions comprising at least one compound of formula (I) represent a further subject-matter of the invention.

According to another of its aspects, it is a further subject-matter of the invention a process for photocuring photopolymerizable compositions and inks, which process comprises:

I) preparing a photopolymerizable composition comprising:
   a) from 15 to 40% by weight, preferably from 20 to 40%, more preferably from 20 to 35% of an ethylenically unsaturated compound dissolved or emulsified in water;
   b) from 0.1 to 10% by weight, preferably from 0.1 to 8% by weight, and more preferably from 0.2 to 6% by weight of at least one compound of Formula (I), as defined above;
   c) from 20 to 80% by weight, preferably from 20 to 75%, more preferably from 30 to 70% of water;

II) optionally pre-drying;

III) photopolymerizing the composition of step I or II with a light source.

Accordingly, a large number of the most varied kinds of light source may be used, the light source emits at wavelengths from approximately 200 nm to approximately 600 nm, for instance from 200 to 450 nm. Both point sources and planiform radiators (lamp carpets) are suitable. Examples are: carbon arc lamps, xenon arc lamps, medium pressure, high pressure and low pressure mercury arc radiators, doped, where appropriate, with metal halides (metal halide lamps), microwave-excited metal vapour lamps, excimer lamps, superactinic fluorescent tubes, fluorescent lamps, argon incandescent lamps, flash lamps, photographic floodlight lamps, light-emitting diodes (LED), electron beams, X-rays and lasers. The distance between the lamp and the substrate according to the invention to be exposed may vary according to the intended use and the type and strength of the lamp and may be, for example, from 1 cm to 150 cm. Particularly preferred are LED light source emitting at wavelengths from 365 nm to 420 nm, preferably 365 nm, 385 nm and 395 nm.

Optionally, said photopolymerizable composition may be applied to a substrate prior to carrying out the photopolymerization step with said light source. Examples of substrates include but are not limited to polyethylene, polypropylene, polyester terephthalate, nylon, paper, board, wood, metal and glass, and other substrates well known to those skilled in the art. Examples of application processes include but are not limited to printing by flexography, gravure, screen, ink jet, lithography, or intaglio, coating by spray, airless spray, rollcoat, flexography, gravure, curtain, cascade, slot, brush and wire-wound roller. Other methods of applying said photopolymerizable composition will be apparent to those skilled in the art.

Said photopolymerizable composition may also be applied over a substrate already comprising a coated or printed layer. Said photopolymerizable composition may, after photopolymerization with said light source, be overprinted or overcoated with one or more compositions suitable for printing or coating.

The article obtained by applying said photopolymerizable composition to said substrate by said means of coating or printing, and photopolymerizing by said light source, with or without further elaboration of the article by further coating or printing, is a further aspect of this invention.

According to a preferred embodiment, in the photopolymerizing process, the compound of Formula (I) is as defined in the preferred embodiments above disclosed.

Surprisingly, we found that compounds of Formula (I) showed a reactivity superior to Omnirad 819 DW (45% wt in water) in water based inkjet ink when used in the same weight amount per active content, with LED lamps while in all the others formulations the reactivity is comparable. Moreover, the new compounds are soluble in all systems, that means that they can be used also in application where a microfiltration is necessary while a water dispersion like Omnirad 819 DW (bis(2,4,6-trimethylbenzoyl)phenylphosphine oxide) is impossible to use. This feature represent a further technical advantage of the invention.

EXAMPLES

Example 1

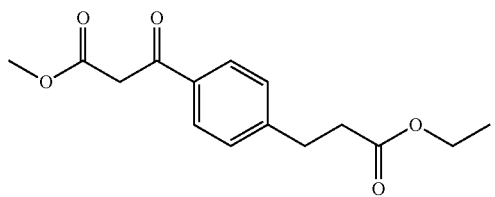 [SMILES: CCOC(=O)CCc1ccc(C(=O)CC(=O)OC)cc1]

Under nitrogen atmosphere 67.0 g (502.5 mmoles) of aluminum chloride were added in small portions under stirring at 0° C. to a solution of 30.0 g (168.3 mmoles) of ethyl 3-phenylpropionate and 24.0 g (175.8 mmoles) of methyl 3-chloro-3-oxopropionate in 250 mL of dichloromethane. After stirring at room temperature for 4 hours, the reaction was poured in ice and water and the resulting mixture was kept under stirring for 30 minutes. Then the organic phase was separated, washed with water, dried over sodium sulfate, filtered and the solvent removed by distillation under vacuum obtaining 37.7 g of a yellow oil (yield 80%).

$^1$H-NMR (CDCl$_3$, δ ppm): 1.22 (t, 3H), 2.65 (t, 2H), 3.05 (t, 2H), 3.75 (s, 3H), 3.98 (s, 2H), 4.10 (q, 2H), 7.30 (d, 2H), 7.85 (d, 2H).

Example 2

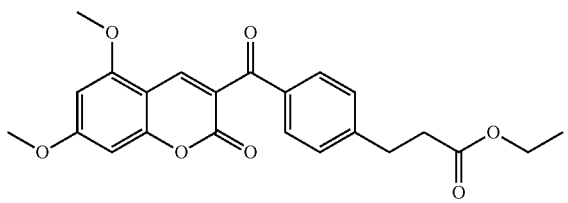 [SMILES: CCOC(=O)CCc1ccc(C(=O)c2cc3c(OC)cc(OC)cc3oc2=O)cc1]

34.1 g (122.5 mmoles) of Example 1 and 0.86 g (10.1 mmoles) of piperidine were added to a solution of 22.3 g (122.4 mmoles) of 4.6-dimethoxy-2-hydroxy-benzaldehyde in 100 mL of ethanol. The mixture was stirred for 2 hours under reflux, then cooled to room temperature. The reaction product was recovered by filtration obtaining 25.0 g of a white-yellow solids (yield 50%).

$^1$H-NMR (CDCl$_3$, δ ppm): 1.23 (t, 3H), 2.65 (t, 2H), 3.10 (t, 2H), 3.89 (m, 6H), 4.12 (q, 2H), 6.30 (d, 1H), 6.45 (d, 1H), 7.30 (d, 2H), 7.79 (d, 2H), 8.40 (s, 1H).

Example 3

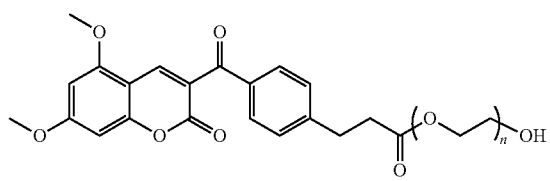

1.27 g (6.08 mmoles) of butyltin hydroxide oxide hydrate were added in small portions under stirring at 150° C. to a mixture of 2.50 g (6.09 mmoles) of Example 2 and 4.87 g (12.18 mmoles) of poly(ethylene glycol) 400. The mixture was stirred at 150° C. for 8 hours eliminating ethanol by distillation. After cooling to room temperature, the reaction mixture was dissolved in dichloromethane and filtered. The filtrate was washed twice with water, dried over sodium sulfate and the solvent removed by distillation under vacuum. The crude product was purified by flash column chromatography on silica gel (dichloromethane:methanol 95:5) obtaining 3.95 g of a yellow-brown oil (yield 85%).

$^1$H-NMR (CDCl$_3$, δ ppm): 2.70 (t, 2H), 3.00 (t, 2H), 3.50-3.70 (m, 32H), 3.90 (m, 6H), 4.20 (t, 2H), 6.30 (d, 1H), 6.45 (d, 1H), 7.30 (d, 2H), 7.75 (d, 2H), 8.40 (s, 1H).

Example 4

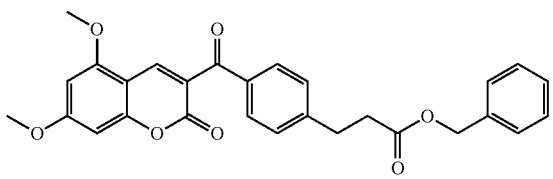 [SMILES: COc1cc(OC)c2cc(C(=O)c3ccc(CCC(=O)OCc4ccccc4)cc3)c(=O)oc2c1]

2.54 g (12.16 mmoles) of butyltin hydroxide oxide hydrate were added in small portions under stirring at 150° C. to a mixture of 5.00 g (12.18 mmoles) of Example 2 and 10.00 g (92.47 mmoles) of benzyl alcohol. The mixture was stirred at 150° C. for 8 hours eliminating ethanol by distillation. After cooling to room temperature, the reaction mixture was diluted with 30 mL of ethanol and the precipitate was recovered by filtration. The precipitate was purified by flash column chromatography on silica gel (toluene:ethyl acetate 90:10) obtaining 5.00 g of a white solid (yield 87%).

$^1$H-NMR (CDCl$_3$, δ ppm): 2.70 (t, 2H), 3.05 (t, 2H), 3.90 (m, 6H), 5.12 (s, 2H), 6.30 (d, 1H), 6.45 (d, 1H), 7.25-7.40 (m, 7H), 7.75 (d, 2H), 8.4 (s, 1H).

Example 5

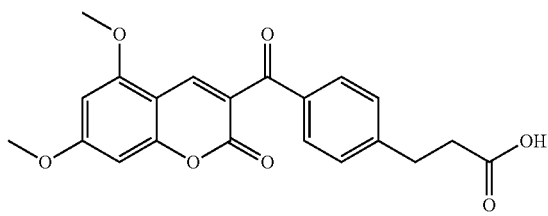 [SMILES: COc1cc(OC)c2cc(C(=O)c3ccc(CCC(=O)O)cc3)c(=O)oc2c1]

20 mL of 6M hydrochloric acid aqueous solution was added to a solution of 2.44 g (5.16 mmoles) of Example 4 in 20 mL of 1,4-Dioxane. The mixture was stirred for 1 hour under reflux, then cooled to room temperature and the solvent removed by distillation under vacuum. The residue was suspended in 25 mL of dichloromethane, heated for 1 hour under reflux and then cooled to room temperature. The reaction product was recovered by filtration obtaining 1.58 g of a white-orange solid (yield 80%).

$^1$H-NMR (CDCl$_3$, δ ppm): 2.72 (t, 2H), 3.02 (t, 2H), 3.90 (m, 6H), 6.30 (d, 1H), 6.45 (d, 1H), 7.30 (d, 2H), 7.80 (d, 2H), 8.42 (s, 1H).

Example 6

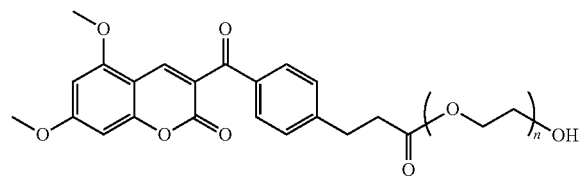

1.27 g (6.08 mmoles) of butyltin hydroxide oxide hydrate were added in small portions under stirring at 150° C. to a mixture of 2.50 g (6.09 mmoles) of Example 2 and 8.22 g (13.70 mmoles) of poly(ethylene glycol) 600. The mixture was stirred at 150° C. for 8 hours eliminating ethanol by distillation. After cooling to room temperature, the reaction mixture was dissolved in dichloromethane and filtered. The filtrate was washed twice with water, dried over sodium sulfate and the solvent removed by distillation under vacuum. The crude product was purified by flash column chromatography on silica gel (dichloromethane:methanol 90:10) obtaining 5.11 g of a yellow-brown oil (yield 87%).

$^1$H-NMR (CDCl$_3$, δ ppm): 2.68 (t, 2H), 3.00 (t, 2H), 3.55-3.70 (m, 50H), 3.88 (d, 6H), 4.20 (t, 2H), 6.29 (d, 1H), 6.42 (d, 1H), 7.30 (d, 2H), 7.75 (d, 2H), 8.40 (s, 1H).

Example 7

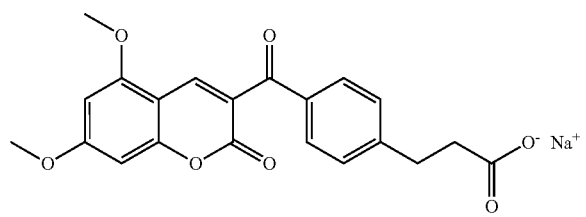 [SMILES: COc1cc(OC)c2cc(C(=O)c3ccc(CCC(=O)[O-])cc3)c(=O)oc2c1 ; [Na+]]

0.549 g (6.53 mmoles) of sodium hydrogencarbonate were added to a suspension of 2.50 g (6.54 mmoles) of Example 5 in 40 mL of ethanol. The mixture was stirred at 80° C. for 1 hour and the solvent removed by distillation under vacuum obtaining 2.64 g of a white solid (yield 100%).

$^1$H-NMR (D$_2$O-DMSO-d$_6$, δ ppm): 2.60 (t, 2H), 3.10 (t, 2H), 4.10 (d, 6H), 6.68 (s, 1H), 6.80 (s, 1H), 7.65 (d, 2H), 7.90 (d, 2H), 8.50 (s, 1H).

Example 8

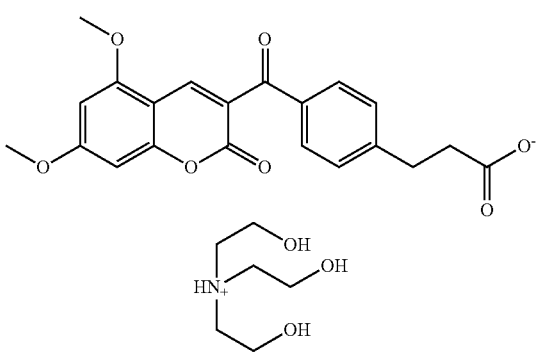

0.975 g (6.54 mmoles) of triethanolamine were added to a suspension of 2.50 g (6.54 mmoles) of Example 5 in 40 mL of ethanol. The mixture was stirred at 80° C. for 1 hour and the solvent removed by distillation under vacuum obtaining 3.37 g of a white solid (yield 97%).

$^1$H-NMR (D$_2$O-DMSO-d$_6$, δ ppm): 2.65 (t, 2H), 3.15 (t, 2H), 3.30 (m, 6H), 3.95 (m, 6H), 4.09 (s, 3H), 4.11 (s, 3H), 6.66 (s, 1H), 6.75 (s, 1H), 7.65 (d, 2H), 7.90 (d, 2H), 8.45 (s, 1H).

Example 9

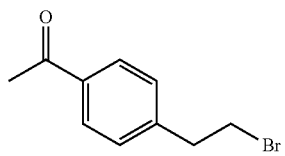

4.23 mL (59.44 mmoles) of acetyl chloride and 10.00 g (54.04 mmoles) of (2-Bromoethyl)benzene were added in sequence at 0° C. to a stirred suspension of 7.93 g (59.47 mmoles) of aluminium chloride in 50 mL of dichloromethane. After stirring at room temperature for 3 hours, the reaction was poured in ice and water and the resulting mixture was kept under stirring for 15 minutes. Then the organic phase was separated, washed with water, dried over sodium sulfate, filtered and the solvent removed by distillation under vacuum obtaining 11.38 g of a pale yellow oil (yield 93%), that was used directly in the next step.

Example 10

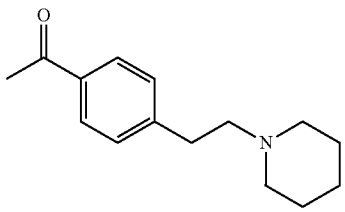 [SMILES: CC(=O)c1ccc(CCN2CCCCC2)cc1]

A solution containing 6.00 g (26.42 mmoles) of Example 9 in acetonitrile (20 mL) was slowly added under stirring at 50° C. to a mixture containing 4.50 g (52.85 mmoles) of piperidine, 4.75 g (34.37 mmoles) of potassium carbonate and 0.44 g (2.65 mmoles) of potassium iodide in 80 mL of acetonitrile. After stirring under reflux for 6 hours, the reaction was cooled to room temperature and the solvent removed by distillation under vacuum. The residue was taken up in ethyl acetate and washed with water. The organic phase was separated, dried over sodium sulfate, filtered and the solvent removed by distillation under vacuum. The crude product was purified by flash column chromatography on silica gel (dichloromethane:methanol 90:10) obtaining 3.25 g of a yellow oil (yield 53%).

$^1$H-NMR (CDCl$_3$, δ ppm): 1.42 (m, 2H), 1.60 (m, 4H), 2.45 (m, 4H), 2.52 (s, 3H), 2.55 (m, 2H), 2.85 (m, 2H), 7.25 (d, 2H), 7.85 (d, 2H).

Example 11

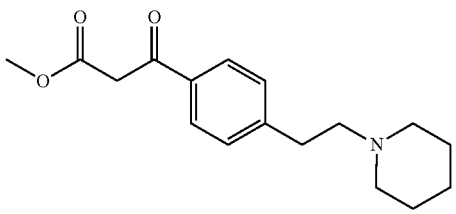 [SMILES: COC(=O)CC(=O)c1ccc(CCN2CCCCC2)cc1]

4.34 g (24.12 mmoles) of sodium methoxide solution at 30% in methanol were dropped under stirring at 90-95° C. to a mixture of 4.65 g (20.10 mmoles) of Example 10 and 18.11 g (201.04 mmoles) of dimethyl carbonate in 30 mL of toluene. The mixture was stirred at 90-95° C. for 4 hours eliminating methanol by distillation. After cooling to room temperature, 60 mL of 12% HCl aqueous solution and 40 mL of water were added in sequence to the reaction. Then the water phase was separated, basified to pH=7.4 with sodium hydrogen carbonate saturated solution and extracted with ethyl acetate. The organic phase was separated, washed with water, dried over sodium sulfate, filtered and the solvent removed by distillation under vacuum obtaining 4.29 g of a yellow oil (yield 74%).

$^1$H-NMR (CDCl$_3$, δ ppm): 1.45 (m, 2H), 1.62 (m, 4H), 2.45 (m, 4H), 2.59 (m, 2H), 2.88 (m, 2H), 3.75 (s, 3H), 3.96 (s, 2H), 7.30 (d, 2H), 7.85 (d, 2H).

Example 12

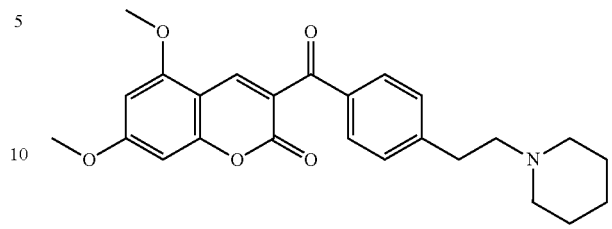

4.20 g (14.51 mmoles) of Example 11 and 0.13 g (1.49 mmoles) of morpholine were added to a solution of 2.64 g (14.49 mmoles) of 4.6-dimethoxy-2-hydroxy-benzaldehyde in 20 mL of ethanol. The mixture was stirred for 2 hours under reflux, then cooled to room temperature. The reaction product was recovered by filtration obtaining 4.33 g of an off-white solid (yield 71%).

$^1$H-NMR (CDCl$_3$, δ ppm): 1.50 (m, 2H), 1.75 (m, 4H), 2.62 (m, 4H), 2.75 (m, 2H), 3.00 (m, 2H), 3.88 (s, 3H), 3.89 (s, 3H), 6.27 (s, 1H), 6.45 (s, 1H), 7.30 (d, 2H), 7.87 (d, 2H), 8.40 (s, 1H).

Example 13

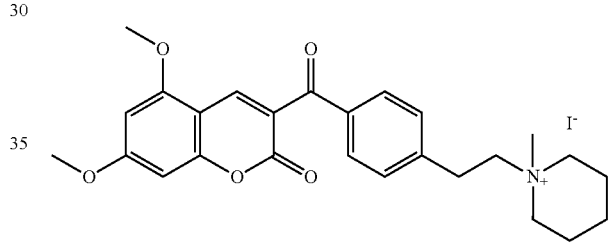

4.64 g (32.69 mmoles) of iodomethane were added under stirring at 35° C. to a solution of 3.00 g (7.12 mmoles) of Example 12 in 200 mL of acetonitrile. After stirring at 35° C. for 2.5 hours, the reaction was cooled to room temperature and the solvent removed by distillation under vacuum. The residue was taken up in ethyl acetate and the precipitate recovered by filtration obtaining 4.00 g of a pale yellow solid (yield 100%).

$^1$H-NMR (DMSO-d$_6$, δ ppm): 0.75 (m, 2H), 1.00 (m, 4H), 2.29 (s, 3H), 2.32 (m, 2H), 2.57 (m, 4H), 2.77 (m, 2H), 3.09 (s, 3H), 3.10 (s, 3H), 5.75 (s, 1H), 5.90 (s, 1H), 6.67 (d, 2H), 7.00 (d, 2H), 7.45 (s, 1H).

Example 14

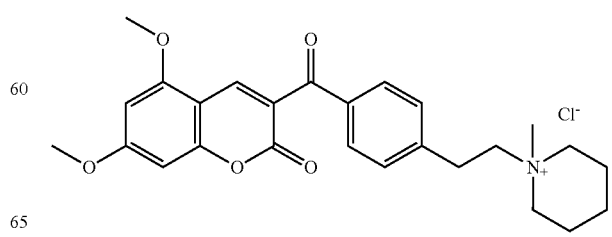

2.54 g (17.72 mmoles) of silver chloride were added under stirring to a mixture of 2.00 g (3.55 mmoles) of Example 13 in 130 mL of methanol. After stirring under reflux for 8 hours in the dark, the reaction was cooled to room temperature, filtered and the solvent removed by distillation under vacuum obtaining 1.68 g of a pale yellow solid (yield 100%).

$^1$H-NMR (DMSO-$d_6$, δ ppm): 0.75 (m, 2H), 1.00 (m, 4H), 2.29 (s, 3H), 2.32 (m, 2H), 2.57 (m, 4H), 2.77 (m, 2H), 3.09 (s, 3H), 3.10 (s, 3H), 5.75 (s, 1H), 5.90 (s, 1H), 6.67 (d, 2H), 7.00 (d, 2H), 7.45 (s, 1H).

Example 15

Comparative Tests

The 3-ketocoumarins of the invention, were compared with Omnirad 819 DW (IGM Resins B. V.) (COMP-1)

Example 15.1

Reactivity Test

Example 15.1.1

Water Based Clear Formulation

The photopolymerizable compositions for the test were prepared dissolving the photoinitiators and the co-initiator, triethanolamine, at a concentration of 3% by weight (wt) each in a mixture 99:1 wt of UCECOAT7200 and Ebecryl 350 (Allnex). The reference compound Omnirad 819 DW (45% wt in water) (COMP-1) was dissolved at a concentration of 6.6% by weight to have the same amount of active content.

The photopolymerizable compositions placed in the sample lodgment of a FT-IR (FT-IR 430-Jasco), were exposed to two different sources:
1) a LED source (400 nm) located at a distance of 25 mm from the sample and at an angle of 30°. (Table 1)
2) A Mercury lamp (160 W) located at a distance of 65 mm from the sample and at an angle of 30°. (Table 2)

IR spectra were acquired at constant time intervals during the photopolymerization and the reduction over the time of the area of the peaks at 1408 and 810 cm$^{-1}$ assigned to the acrylic double bonds was determined using the IR software. This allows quantifying the degree of polymerization and therefore the efficiency of the photoinitiator.

The results at 400 nm, expressed as % of polymerization over the time, are reported in Table 1 and the results with the Mercury lamp are reported in Table 2.

TABLE 1

| Example | 0.5 sec | 2 sec |
| --- | --- | --- |
| COMP-1 | 34 | 39 |
| Example 3 | 32 | 37 |
| Example 6 | 34 | 37 |
| Example 8 | 7 | 15 |
| Example 14 | 23 | 27 |

TABLE 2

| Example | 0.2 sec | 1 sec |
| --- | --- | --- |
| COMP-1 | 39 | 45 |
| Example 3 | 33 | 42 |
| Example 6 | 32 | 39 |

TABLE 2-continued

| Example | 0.2 sec | 1 sec |
| --- | --- | --- |
| Example 8 | 9 | 16 |
| Example 14 | 15 | 23 |

Example 15.1.2

Water Based Black Inkjet Ink

The photopolymerizable compositions for the test were prepared by dissolving the photoinitiators and the co-initiator triethanolamine at a concentration of 5.0% wt each in a water based black ink for ink-jet printing. The reference compound Omnirad 819 DW (45% wt in water) (COMP-1) was dissolved at a concentration of 11% by weight to have the same amount of active content.

The photopolymerizable compositions placed in the sample lodgment of a FT-IR (FT-IR 430-Jasco), were exposed to two different sources:
1) a LED source (400 nm) located at a distance of 25 mm from the sample and at an angle of 30°. (Table 3)
2) A Mercury lamp (160 W) located at a distance of 65 mm from the sample and at an angle of 30°. (Table 4)

IR spectra were acquired at constant time intervals during the photopolymerization and the reduction over the time of the area of the peaks at 1408 cm$^{-1}$ and 810 cm$^{-1}$ assigned to the acrylic double bonds was determined using the IR software. This allows quantifying the degree of polymerization and therefore the efficiency of the photoinitiator.

The results at 400 nm, expressed as % of polymerization over the time, are reported in Table 3 and the results with the Mercury lamp are reported in Table 4.

TABLE 3

| Example | 0.5 sec | 2 sec |
| --- | --- | --- |
| COMP-1 | 4 | 13 |
| Example 3 | 48 | 71 |
| Example 6 | 62 | 81 |
| Example 14 | 38 | 62 |

TABLE 4

| Example | 0.2 sec | 1 sec |
| --- | --- | --- |
| COMP-1 | 77 | 88 |
| Example 3 | 77 | 91 |
| Example 6 | 76 | 92 |
| Example 14 | 67 | 89 |

Example 15.1.3

Water Based Clear Inkjet Ink

The photopolymerizable compositions for the test were prepared by dissolving the photoinitiators and the co-initiator triethanolamine at a concentration of 5.0% wt each in a water based clear ink for ink-jet printing. The reference compound Omnirad 819 DW (45% wt in water) (COMP-1) was dissolved at a concentration of 11% by weight to have the same amount of active content. Two different conditions were used:
A. The solution is prepared and stirred at 40° C. for 1 h, then cooled at room temperature and photopolymerized.

B. The solution is prepared and stirred at 40° C. for 1 h, then cooled at room temperature, filtered on a 0.45 μm Millipore filter and photopolymerized.

The photopolymerizable composition, placed in the sample lodgment of a FT-IR (FT-IR 430-Jasco), were exposed to a LED source (400 nm) located at a distance of 25 mm from the sample and at an angle of 30°.

IR spectra were acquired at constant time intervals during the photopolymerization and the reduction over the time of the area of the peaks at 1408 cm$^{-1}$ and 810 cm$^{-1}$ assigned to the acrylic double bonds was determined using the IR software. This allows quantifying the degree of polymerization and therefore the efficiency of the photoinitiator.

The results at 400 nm, expressed as % of polymerization over the time, are reported in Table 5.

TABLE 5

| Example | Test A after 0.5 sec | Test B after 0.5 sec |
| --- | --- | --- |
| COMP-1 | 30 | 15 |
| Example 6 | 64 | 61 |

These tests confirm that compounds of Formula (I) are equal reactive or more reactive than the comparatives (COMP-1) with the advantage to be soluble in the formulation and not dispersed. That means that the compounds of Formula (I) can be used in all applications.

The invention claimed is:

1. A compound of Formula (I)

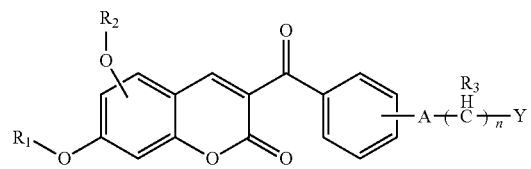

wherein:
$R_1$, $R_2$ are, each independently, hydrogen; $C_1$-$C_{12}$ alkyl; substituted or unsubstituted aryl; substituted or unsubstituted heteroaryl; substituted or unsubstituted $C_5$-$C_6$ cycloalkyl; or $C_1$-$C_{12}$ alkyl which is substituted with SH, —N(alkyl $C_1$-$C_6$)$_2$, piperidino, morpholino, piperazino, —OH, —O(alkyl $C_1$-$C_{12}$), —COOH; or $C_1$-$C_{12}$ alkoxy;

n is an integer number from 0 to 10 and when n is 0 A is directly linked to Y;

A represents CHR$_3$, O, S or NR$_4$ where R$_4$ is hydrogen or an alkyl $C_1$-$C_6$ group;

$R_3$ is hydrogen; $C_1$-$C_{12}$ alkyl; substituted or unsubstituted aryl; substituted or unsubstituted heteroaryl; substituted or unsubstituted $C_5$-$C_6$ cycloalkyl; or $C_1$-$C_{12}$ alkyl which is substituted with SH, —N(alkyl $C_1$-$C_6$)$_2$, piperidino, morpholino, piperazino, —OH, —O(alkyl $C_1$-$C_{12}$), —COOH; or $C_1$-$C_{12}$ alkoxy;

Y is selected from:

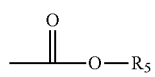

wherein $R_5$ is a substituted or unsubstituted $C_1$-$C_{50}$ alkyl group which is interrupted by one or more oxygens and may terminate with a hydroxy group or with an alkyl residue;

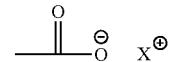

wherein X is an inorganic or organic cation;

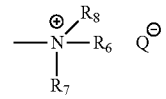

wherein Q is an inorganic or organic anion and $R_6$, $R_7$ and $R_8$ are, each independently, hydrogen; $C_1$-$C_{12}$ alkyl; substituted or unsubstituted aryl; substituted or unsubstituted heteroaryl;
substituted or unsubstituted $C_5$-$C_6$ cycloalkyl; $C_1$-$C_{12}$ alkyl which is substituted with SH, —N(alkyl $C_1$-$C_6$)$_2$, piperidino, morpholino, piperazino, —OH, —O(alkyl $C_1$-$C_{12}$), —COOH; $C_1$-$C_{12}$ alkoxy; or two of R6, R7 and R8, form a mono cyclic ring structure,

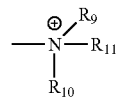

wherein $R_9$, $R_{10}$ and $R_{11}$ are each independently one of another hydrogen, alkyl $C_1$-$C_{12}$, substituted or unsubstituted phenyl, aryl or heteroaryl, cycloalkyl $C_5$-$C_6$, alkyl $C_1$-$C_{12}$ which is substituted with SH, —N(alkyl $C_1$-$C_6$)$_2$, piperidino, morpholino, piperazino, —OH, —O(alkyl $C_1$-$C_{12}$), —COOH; $C_1$-$C_{12}$ alkoxy; or two of $R_9$, $R_{10}$ and $R_{11}$, form a mono cyclic ring structure, and at least one of $R_9$, $R_{10}$ or $R_{11}$ is selected from the following:

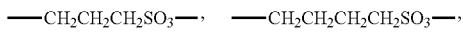
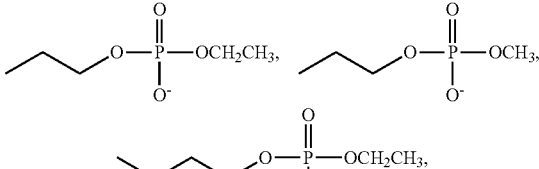
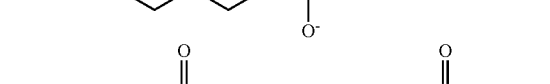
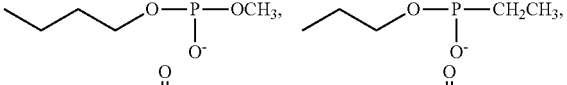
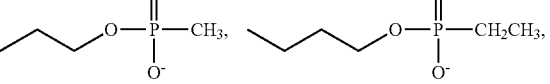
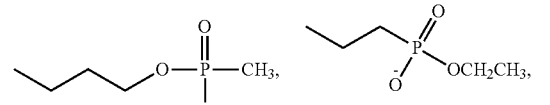

-continued

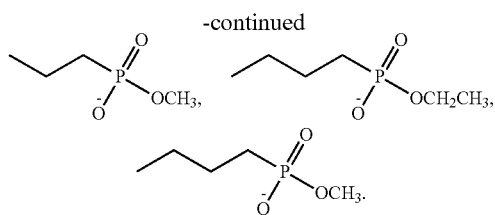

2. The compound of Formula (I) according to claim 1, wherein n is from 0 to 6.

3. The compound of Formula (I) according to claim 1 wherein A is $CHR_3$.

4. The compound of Formula (I) according to claim 1 wherein Y is

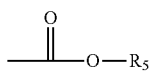

wherein $R_5$ is a substituted or unsubstituted $C_1$-$C_{50}$ alkyl group which is interrupted by one or more oxygens and may terminate with a hydroxy group or with an alkyl residue.

5. The compound of Formula (I) according to claim 1, wherein $R_1$ and $R_2$ are both a methyl group.

6. The compound of Formula (I) according to claim 1, wherein $R_3$ is hydrogen.

7. A photopolymerizable composition which comprise at least one ethylenically unsaturated compound dissolved or emulsified in water and at least one compound of Formula (I) as defined in claim 1, optionally in combination with at least one co-initiator.

8. A process for photopolymerizing, which comprises the following steps:
   I) preparing a photopolymerizable composition comprising:
   a) from 15 to 40% by weight of an ethylenically unsaturated compound dissolved or emulsified in water;
   b) from 0.1 to 10% by weight, of at least one compound of Formula (I), as claimed in claim 1;
   c) from 20 to 80% by weight of water;
   II) optionally pre-drying;
   III) photopolymerizing the composition of step I or II with a light source.

9. The process of claim 8, wherein the photopolymerization is carried out with a LED light source emitting at wavelengths 200 nm to 420 nm.

10. The process of claim 9, wherein the photopolymerization is carried out with a LED light source emitting at wavelengths from 365 nm to 420 nm.

11. The process of claim 8, further comprising the step of applying said photopolymerizable composition to a substrate prior to photopolymerizing it.

12. The process of claim 8, wherein at least one co-initiator is also present.

13. An article of manufacture prepared according to the process of claim 8.

14. The process of claim 8, wherein the photopolymerizable composition comprises from 20 to 40% by weight of an ethylenically unsaturated compound dissolved or emulsified in water.

15. The process of claim 8, wherein the photopolymerizable composition comprises from 20 to 35% by weight of an ethylenically unsaturated compound dissolved or emulsified in water.

16. The process of claim 8, wherein the photopolymerizable composition comprises from 0.1 to 8% by weight of at least one compound of Formula (I) as defined above.

17. The process of claim 8, wherein the photopolymerizable composition comprises from 0.2 to 6% by weight of at least one compound of Formula (I) as defined above.

18. The process of claim 8, wherein the photopolymerizable composition comprises from 20 to 75% of water.

19. The process of claim 8, wherein the photopolymerizable composition comprises from 30 to 70% of water.

20. The process of claim 8, wherein the light source emit at wavelengths from 200 to 600.

* * * * *